(12) United States Patent
Kratzsch et al.

(10) Patent No.: US 9,291,540 B2
(45) Date of Patent: Mar. 22, 2016

(54) DEVICE FOR DETECTING ABRASIVE WEAR

(71) Applicant: Voith Patent GmbH, Heidenheim (DE)

(72) Inventors: Axel Kratzsch, Altheim (DE); Daniel Christ, Heidenheim (DE); Jan Schoppa, Ulm (DE)

(73) Assignee: Voith Patent GmbH, Heidenheim (DE)

( * ) Notice: Subject to any disclaimer, the term of this patent is extended or adjusted under 35 U.S.C. 154(b) by 357 days.

(21) Appl. No.: 14/116,336

(22) PCT Filed: Jan. 7, 2013

(86) PCT No.: PCT/EP2013/050144
§ 371 (c)(1),
(2) Date: Nov. 7, 2013

(87) PCT Pub. No.: WO2013/107664
PCT Pub. Date: Jul. 25, 2013

(65) Prior Publication Data
US 2014/0102199 A1 Apr. 17, 2014

(30) Foreign Application Priority Data
Jan. 20, 2012 (DE) .......................... 10 2012 000 988

(51) Int. Cl.
*G01N 3/56* (2006.01)
*G01H 13/00* (2006.01)
*F03B 11/00* (2006.01)

(52) U.S. Cl.
CPC ................ *G01N 3/56* (2013.01); *F03B 11/008* (2013.01); *G01H 13/00* (2013.01); *F05B 2240/242* (2013.01); *Y02E 10/226* (2013.01)

(58) Field of Classification Search
CPC ........ F03B 11/008; G01N 3/56; G01H 13/00; F05B 2240/242; Y02E 10/226

USPC ............................................ 73/579
See application file for complete search history.

(56) References Cited

U.S. PATENT DOCUMENTS

| 8,616,833 | B2 * | 12/2013 | Dahlhaug | F03B 11/002 415/115 |
| 2008/0192568 | A1 * | 8/2008 | Hielscher | B01F 11/025 366/347 |
| 2009/0314748 | A1 * | 12/2009 | Rao | B23H 7/38 219/69.17 |
| 2011/0014049 | A1 | 1/2011 | Dahlhaug | |
| 2013/0068027 | A1 * | 3/2013 | Sullivan | G01B 17/02 73/628 |

* cited by examiner

FOREIGN PATENT DOCUMENTS

| EP | 1 970 561 | 11/2009 |
| JP | H 08-326645 | 12/1996 |

OTHER PUBLICATIONS

English Translation of PCT International Preliminary Report on Patentability dated Jul. 31, 2014 in PCT Application No. PCT/EP2013/050144.

*Primary Examiner* — J M Saint Surin
(74) *Attorney, Agent, or Firm* — Farjami & Farjami LLP

(57) ABSTRACT

The invention relates to a device for detecting the abrasive wear on components of water turbines, having
  a wearing body, and
  a measuring unit for detecting the wear on the wearing body.
The invention is characterized in that
  the wearing body is arranged in the flow flowing through the water turbine,
  the wearing body is implemented as a sonotrode and is connected to an ultrasound generator, and
  the measuring unit is implemented to measure the resonant frequency of the sonotrode.

20 Claims, 2 Drawing Sheets

DEVICE FOR DETECTING ABRASIVE WEAR

This is a U.S. national phase application, which is based on, and claims priority from, PCT application Serial No. PCT/EP2013/050144, filed Jan. 7, 2013, which claims priority from foreign application Serial No. 10 2012 000 988.7, filed Jan. 20, 2012, in Germany.

The invention relates to a device for detecting abrasive wear on components of water turbines according to the type defined in greater detail in the preamble of Claim 1. Furthermore, the invention relates to a hydroelectric plant having such a device. Finally, the invention additionally relates to a method for detecting the abrasive wear in a hydroelectric plant having such a device.

Components around which water flows, in particular components of the turbine, for example, guide vanes and turbine vanes, are very strongly worn by sediments, which are present in the flowing water. This erosion of components around which water flows in hydroelectric plants by the sediments entrained in the flow is a very great problem in particular in South American countries and in India, and also in the Alpine region. On the one hand, this abrasive wear on components of the water turbine caused by the sediments causes additional maintenance work and a reduced efficiency of the water plant. This is sometimes linked to very high economic losses for the operator. On the other hand, geometries of the wearing components can be changed with time by the abrasive wear. This can result in substantial safety risks due to a reduction of wall thicknesses and vibrations resulting therefrom. In addition to wear of guide vanes and turbine vanes, wear of the seals in the region of the water turbine typically additionally arises due to the sediments. These seals, which are normally embodied as labyrinth seals, also represent components of the water turbine which are subject to elevated wear. The embodiments described hereafter also apply similarly for them. Excess wear of a seal can result in increased friction and/or undesired leaks in the region of the turbine.

Up to this point, the knowledge about the wear status of a water turbine has typically been based on long-term experience of the operator of the hydroelectric plant. A direct status check is typically only possible if the water turbine has a planned shutdown in any case for maintenance purposes and is opened as a whole. However, a status check by an additional shutdown of the water turbine would be very costly outside of planned maintenance shutdowns.

A further set of problems in the estimation of the abrasive wear is that values can be transferred hardly or not at all from one plant to another plant. The quantity and the composition of the sediment entrained in the water differs greatly by region and is subject to strong temporal and seasonal variations. The quantity and type of the sediment is additionally dependent on geological, topographic, and climatic boundary conditions. This makes an estimation extraordinarily difficult. An indirect inference of the wear on components of the water turbine, for example, by a sediment measurement, is also extraordinarily complex and subject to very great uncertainties and errors.

European patent application EP 1 970 561 A1 therefore attempts to specify a device which detects the wear state of the water turbine via test bodies in a parallel flow path of the water charged with sediment and studies these test bodies via cameras or other measuring methods (not specified in greater detail), for example, in order to allow indirect inferences about the wear of the components of the water turbine. For this purpose, the wear is determined on test bodies to which sediment-containing water is applied via a bypass. The disadvantage is that this bypass requires a pressure drop for a forced through-flow. Therefore, complex modifications are necessary for a measuring chamber having regulated water supply. The quantity of water removed from the flow must additionally be discharged again appropriately after it is incident on the test body. In order to achieve this, the arrangement is provided as a bypass in the region of the pressure line, the so-called penstock. However, this represents a further disadvantage, since the abrasion on the test body is very strongly dependent on the location of the water removal in the penstock. This is of decisive significance, since the location of the water removal is decisive for the quantity of sediment, since this sediment is typically not uniformly distributed in the pressure line. Interpreting the results is thus accordingly difficult. A further problem is that the results are very strongly dependent on the set pressure drop within the measuring arrangement.

Furthermore, a water removal from the pressure line is rather critical with respect to the strength and functionality of the pressure line. Such a water removal from the pressure line can only be installed later in an existing structure with extremely high expenditure, but rather must also be planned from the beginning because of the complex structural situation and a suitable pressure line implemented for this purpose. The method is therefore very complex and nonetheless quite imprecise.

A further disadvantage of the structure described in the European patent application is that it is not capable of reacting to different operating states, i.e., different load states of the water turbine. The water quantity which is incident on the test body is dependent in the bypass, in the case of removal from the penstock, only on the pressure difference between the penstock and the measuring chamber and the cross-section of the bypass outlet or the nozzle outlet, respectively. Additional regulation, for example, in the event of part load of the water turbine, is not possible or is only possible by way of an additional valve which can be activated actively as a function of the load state of the water turbine. This is accordingly complex and further increases the hazard of inaccuracies.

The object of the present invention is thus to provide a device for detecting the abrasive wear on components of water turbines, which avoids these disadvantages and permits simple, efficient, and reliable inferences about the wear in the region of the components of the water turbine.

This object is achieved according to the invention with a device which has the features in the characterizing part of Claim 1. A hydroelectric plant having such a device is additionally specified in Claim 8. Furthermore, a method for detecting the abrasive wear as defined in the invention is specified in Claim 14. Advantageous refinements and embodiments of the device, the hydroelectric plant, and the method result from the dependent subclaims.

The solution according to the invention of the device for detecting the abrasive wear provides a wearing body, which is arranged directly in the flow which flows through the water turbine. The wearing body therefore always has precisely the water in the quantity and composition applied to it as the corresponding components of the turbine also do, the wear of which is to be concluded. The wearing body itself is implemented as a sonotrode and is connected to an ultrasound generator. Such a wearing body implemented as a sonotrode of an ultrasonic sensor has the decisive advantage that the resonant frequency of the ultrasonic sensor increases accordingly as a function of a mass reduction at the sonotrode. Thus, the abrasion on the wearing body which forms the sonotrode can be measured directly and immediately via a measuring unit for measuring the resonant frequency for the sonotrode.

By suitable wearing bodies and because of the arrangement of the wearing body in precisely the flow in which the components of the turbine are also located, a very precise and reliable measurement can thus be achieved. The sonotrode only experiences the abrasion which is also actually produced by sediments reaching the water turbine. A correlation of the abrasion of the sensor and the components is therefore possible very simply and reliably. The correlation can be performed, for example, by a comparison of the component abrasion to the abrasion of the sonotrode in the context of inspections occurring in any case. However, it may also be carried out by means of comparative CFD calculations. In this case, the abrasion behavior of the sonotrode is calculated in comparison to the abrasion behavior on the component. The sonotrode abrasion is used as a calibration measure for the abrasion calculation on the component.

In a particularly favorable and advantageous embodiment of the device according to the invention, it is provided that the sonotrode protrudes into the flow flowing out of the water turbine. In particular the flow after the water turbine, i.e., in the region of the so-called suction pipe of a hydroelectric plant, contains a comparable composition of sediments and water in comparison to the pressure line in approximately every section of its cross-section. In addition, the flow also still has a very high flow velocity even after the turbine. Therefore, the installation of the sonotrode of the device according to the invention in this region is particularly advantageous. A further advantage is that the structural safety-relevant pressure line remains untouched and the installation of the sonotrode is performed in the region after the turbine, with correspondingly lower pressure level.

The sonotrode itself can be, according to an advantageous embodiment of the device according to the invention, formed from a cylindrical wearing body having an attachment element for the connection to the ultrasound generator. This cylindrical structure, which in particular can also have a spherical end on the side facing away from the ultrasound generator, is particularly simple and efficient and is comparatively insensitive with respect to larger parts in the flow, for example, entrained stones or branches which pass through the turbine. Nonetheless, of course, other shapes of the sonotrode, for example, a hollow cylinder or a wing-shaped embodiment, are also conceivable and possible.

The sonotrode itself can, according to a particularly favorable and advantageous embodiment of the device according to the invention, consist of a steel material, in particular chromium-nickel steel or chromium-nickel-molybdenum steel. Such a structure made of a steel material, in particular the material from which the components of the turbine are also manufactured, permits a good inference about the abrasion of the components of the water turbine in relation to the abrasion in the region of the sonotrode because of the approximately identical wearing characteristic. Preferred materials can be steels having the numbers 1.4313 or 1.4317 here, for example.

In an alternative embodiment of the device according to the invention, however, it can also be provided that the sonotrode is formed from a nonferrous material, in particular from an aluminum or copper alloy. Such aluminum or copper alloys have a substantially lower abrasion resistance than the typically used steel materials of the water-guiding components of the water turbine. This allows a higher temporal resolution of the abrasion for the measurement. This is advantageous in particular if the damaging effect of individual events, for example, a flood, an intentional drainage of sediments through the turbine, a function reduction or a function failure of a sand trap or the like, for example, is to be detected.

Because of the more rapid abrasion in the region of the wearing body of the sensor in relation to the water-guiding components, a higher resolution of the measurement is possible, whereby such individual events can also be detected much more easily.

Furthermore, in another embodiment of the device according to the invention, it can be provided that the sonotrode is at least partially provided with a carbide coating. Such carbide coatings have become common in the meantime, in order to secure the steel components of the water turbine as long as possible against wear, for example. If such components are used, it can then be particularly advantageous if the sonotrode is also implemented accordingly, in order to reproduce the wearing characteristic of the components of the turbines as precisely as possible, for example. In addition, the service lives of the coatings in the region of the water turbines can be detected via such a coated sonotrode and the required maintenance can be preplanned based on the measured values. This is true in particular if the carbide coating is applied to a material which is otherwise abraded very rapidly, for example, to a sonotrode constructed from an aluminum alloy or from bronze. As long as the carbide layer is undamaged, a very low level of abrasion occurs. In the event of damage to the carbide coating, the abrasion rate, and therefore the resonant frequency of the sonotrode, suddenly rises. This may be detected very easily and reliably.

In the hydroelectric plant according to the invention, it is provided that it has at least one water turbine, which is arranged between a pressure pipe upstream of the water turbine in the flow direction and a suction pipe downstream of the water turbine in the flow direction. In addition to the at least one water turbine, of course, further water turbines can also be provided. In addition, the power plant according to the invention has at least one device for detecting the abrasive wear according to the type specified above. Such a device for detecting the abrasive wear can be arranged in particular in the region of each of the water turbines or also in the region of only one water turbine, if it is to be expected that the water turbines, if a plurality thereof are provided, have incident flow with water and sediment in the same composition. Furthermore, it is possible, of course, if a homogeneous distribution of water and sediment is not to be expected, for example, if the device for detecting the abrasive wear is installed in the region of the pressure pipe, that a plurality of such sonotrodes are distributed over the circumference and a certain running length of the pressure pipe, in order to obtain comparatively good inferences about the wear of the water turbine by averaging or weighted averaging, for example.

In a particularly favorable embodiment of the hydroelectric plant according to the invention, in contrast, it is provided that the sonotrode of the device is arranged in the suction pipe. Such an arrangement in the suction pipe, i.e., downstream of the water turbine, is particularly advantageous, since the pressure conditions are much more favorable here for introducing an opening into the suction pipe and for sealing this opening around the sonotrode. In the case of an arrangement, in particular comparatively closely downstream of the turbine, the flow velocities are nonetheless sufficiently high that a reliable value for the wear is achieved. In addition, the water is very well mixed with the sediments downstream of the turbine, so that approximately the same distribution of the sediments in the water is provided overall in the region of the suction pipe.

In a particularly favorable embodiment thereof, the sonotrode can be arranged at a short distance, preferably less than 2-3 m, in the flow direction downstream of the water turbine. This comparatively short distance for the transition between the water turbine and the suction pipe is of decisive advantage, since the flow conditions, in particular the velocity downstream of the turbine, is still sufficiently high here that reliable measuring results are to be expected. In the further course of the suction pipe, with greater distance of the sonotrode from the water turbine, worsening of the measured values is to be expected. The causes of this are, on the one hand, increasing sinking of the sediments downward in the water flow, the further the flow moves away from the turbine. In addition, the flow velocity reduces with increasing distance from the turbine. Since the flow velocity has a substantial influence on the abrasion, a reduction of the flow velocity in the region of the sonotrode is possibly to be counteracted by the arrangement at the shortest possible distance downstream of the water turbine.

In a further very advantageous embodiment of the hydroelectric plant according to the invention, it is additionally provided that the sonotrode is arranged downstream of a flow divider. Such a flow divider or splitter, which can be implemented as a sheet-metal element in the region of the suction pipe in the flow direction upstream of the sonotrode, for example, can keep coarser parts such as rocks, branches, and the like away from the sonotrode and deflect them from the sonotrode. Nonetheless, the sediment-containing water washes around the sonotrode and thus permits very reliable detection of the abrasive wear without the hazard of structural damage.

Alternatively or additionally to the flow divider, it can also be provided that the sonotrode is arranged in a pipe section through which the flow flows inside or parallel to the suction pipe. Such a pipe section can be implemented, according to an advantageous embodiment, in particular as a half pipe, which is fastened on the wall of the suction pipe. Good protection of the sonotrode from rocks, branches, and the like is thus ensured and nonetheless sediment-charged water flows around it safely and reliably with the same flow conditions and the same velocity as the remainder of the suction pipe. Fundamentally, it is also conceivable to branch off a pipe section from the suction pipe and to guide it parallel thereto. However, this is structurally more complex.

A method according to the invention for detecting the abrasive wear in a hydroelectric plant according to one of the described embodiments now provides that, by means of the measuring device, the resonant frequency of the sonotrode is measured, wherein a resonant frequency which rises because of the material abrasion on the sonotrode is used as a measure of an increasing wear of components of the water turbine of the hydroelectric plant. This method corresponds to the preferred intended use already described above in the case of the device. The method allows a safe and reliable statement about the wear in the region of the components of the water turbine by an inference based on the wear in the region of the sonotrode. Since the resonant frequency of the sonotrode can be measured simply and efficiently, an uninterrupted measurement is possible, as is a measurement at predefined time intervals. These can be selected correspondingly closely or also as a longer time interval. Because of the abrasion of the material of the sonotrode, the measured resonant frequency changes from measurement to measurement or over time, for example. A rising resonant frequency at the sonotrode is then a suitable measure for the wear of the sonotrode and permits very precise inferences about the wear of the components of the water turbine, around with water and sediment flow under the same flow conditions. A continuous observation of the wear state is therefore possible, so that maintenance intervals can accordingly be planned early and in particular can be consolidated with maintenance which is upcoming in any case. Failures of the water turbine can therefore be prevented and maintenance costs can be reduced because of the possible optimization and consolidation of routine maintenance and wear-related maintenance.

In a particularly favorable embodiment of the method according to the invention, it is additionally provided that a measuring signal, which is correlated with the wear, is transmitted to a remote maintenance unit. The incorporation of the sensor signal in an automation unit of the hydroelectric plant is obvious. Now, it is also possible to incorporate a measuring signal, which is correlated with the wear, via a remote maintenance unit or a remote control, i.e., the remote operation of the power plant, for example, via Internet connection, and to transmit the measuring signal correlated with the wear to the remote maintenance unit. In this way it is possible to perform an analysis of the corresponding signal independently of the location of the power plant. An incorporation in the remote maintenance can thus be implemented with possibly very complex and frequently updating software in the region of the remote maintenance unit. In addition, necessary maintenance work can be coordinated in the scope of the remote maintenance. For example, it can be part of a service contract, in the case of which the service contract partner has access, via the remote maintenance, to the corresponding wear data or to the measured values correlated thereto at any time and at any arbitrary location.

Further advantageous embodiments of the device according to the invention and a hydroelectric plant according to the invention and the method according to the invention result from the remaining dependent subclaims and will be clear on the basis of the exemplary embodiment, which is described in greater detail hereafter with reference to the figures.

Figure 1:
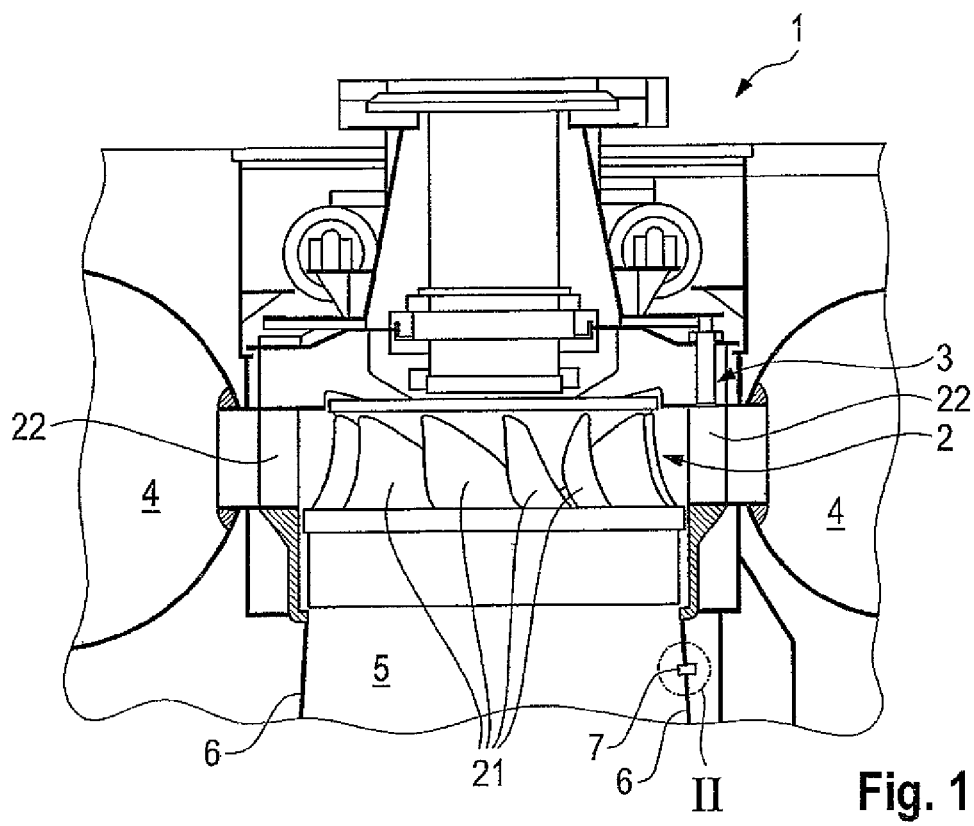
FIG. 1 shows a detail of a hydroelectric plant according to the invention.

A detail of a hydroelectric plant 1 is indicated as an example in the illustration of FIG. 1. The core of this hydroelectric plant 1 is a water turbine 2, which is implemented here, for example, as a Francis turbine. The Francis turbine is to be understood solely as an example. The invention would also be conceivable in the case of all other types of turbines, for example, a Kaplan turbine, a Pelton turbine, or the like, in the above-described manner. A person skilled in the art can readily transfer this exemplary embodiment described based on the Francis turbine to other types of hydroelectric plants.

The water turbine 2 comprises, in addition to seals, substantially two further types of components around which water flows. These are, on the one hand, the turbine vanes 21, of which only a few are provided with a reference sign here. In addition, there are so-called guide vanes 22, which control the supply of the water to the turbine vanes 21. The water enters the turbine 2 from a pressure line 4 through the vane ring 3, which is formed by the guide vanes 22 and encloses the turbine 2. Only two parts of a ring line, which encloses the vane ring 3 and connects the pressure line 4 to the turbine 2, can be recognized here in sections of the pressure line 4. A so-called section line 5, of which a part of the walls 6 can be recognized, follows downstream of the water turbine 2 in the flow direction of the water.

Depending on the geographic region and boundary conditions, a mixture of water and a specific quantity of sediment flows through the water turbine 2. Due to this sediment, as explained at the beginning, wear occurs in the region of the components 21, 22 of the water turbine 2 around which water flows. In order to detect this wear, a device 7 for detecting the abrasive wear is schematically indicated in the illustration of FIG. 1. This device 7, which is enclosed by a circle in the illustration of FIG. 1, can be seen in the illustration of FIG. 2 enlarged once again in a schematic view as the detail of FIG. 1 designated with II.

Figure 2:
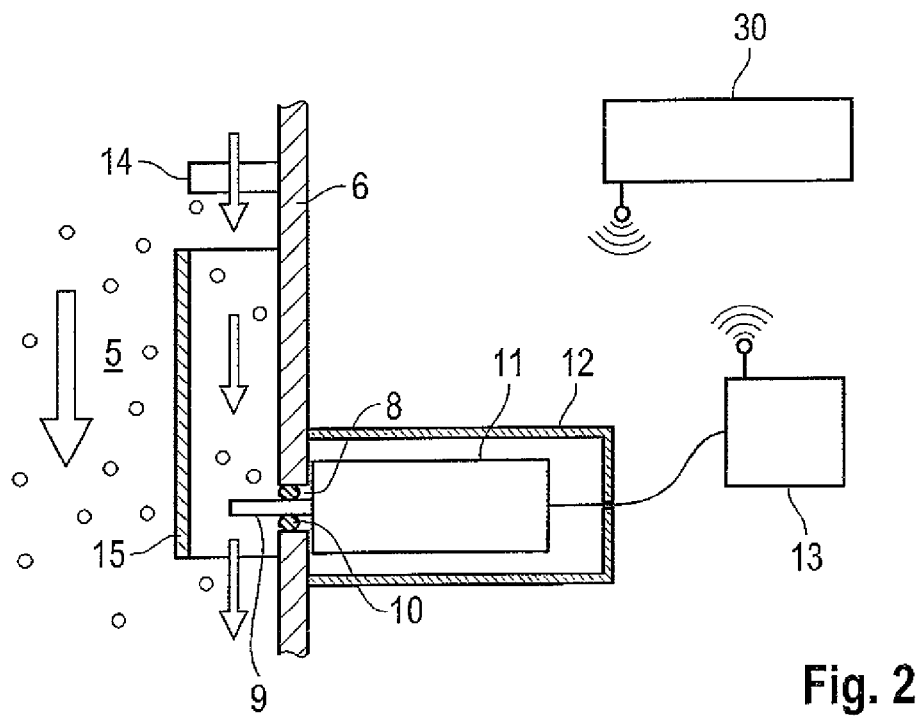
FIG. 2 shows an enlarged schematic view of the device for detecting the abrasive wear.

The suction pipe wall 6 has an opening 8, through which a wearing body 9 protrudes through a seal 10 into the interior of the suction pipe 6. The wearing body 9 is connected at its other end to an ultrasound generator 11, which is inserted into a housing 12 in the exemplary embodiment shown here. This housing can be placed in the region of the wall 6 of the suction pipe 5 such that simple replacement of the wearing body 9 and the sensor is also readily possible in operation of the plant. The ultrasound generator 11 is connected to a frequency generator, which can simultaneously be used as a measuring unit 13. This measuring unit 13 detects the resonant frequency of the wearing body 9, which is implemented as a sonotrode and is connected to the ultrasound generator 11. If abrasive wear occurs in the region of this sonotrode 9, the resonant frequency rises with increasing loss of mass. A rising resonant frequency is thus correlated with increasing wear. The sonotrode 9 protrudes into the interior of the suction pipe 6 and precisely the quantity and composition of sediment-charged water washes around it as the components 22, 23 of the water turbine 2. Via the measuring unit 13, which is incorporated in particular in automation electronics of the hydroelectric plant 1, the analysis can be performed, which is then made accessible for data processing. Additionally or alternatively thereto, the data can also be transmitted to a remote maintenance unit 30. The remote maintenance unit 30 is schematically indicated in the illustration of FIG. 2 and can communicate, for example, via a data line or, as indicated here, via a radio signal with the measuring unit or with the automation technology of the hydroelectric plant 1, which is superior to the measuring unit 13. The communication with respect to the wear can be performed, on the one hand, with the wear signal which is already analyzed or, alternatively thereto, in that the signal transmits the resonant frequency and is analyzed independently of the location of the hydroelectric plant 1 in the region of the remote maintenance. The wear can therefore be incorporated in remote operation of the power plant and can be incorporated in maintenance plans prepared in the region of the remote maintenance, a maintenance service contract, or the like.

In order to prevent the damage of the sonotrode 9 by larger parts, for example, rocks or branches, which have passed the turbine 2, a flow divider or splitter 14 or a half pipe 15 or optionally also both can optionally be provided. In this way, a flow arises in the region of the sonotrode 9 which only carries water and sediments with it, larger interfering parts are diverted by the half pipe 15 and/or the flow splitter 14. The half pipe 15 and the flow splitter 14 are each conceivable and possible alone. Of course, a structure as shown in FIG. 2 is also conceivable and possible. By way of the combination of the flow splitter 14 with the half pipe 15, a structure results which is implemented as very secure in relation to jamming rocks, sticks, and the like. The illustration in FIG. 2 is to be understood solely as an example, since the distance between the flow splitter 11 and the intake of the half pipe 15 must be adapted in accordance with the flow conditions and is shown rather too small in the schematic illustration selected in FIG. 2.

Figure 3:
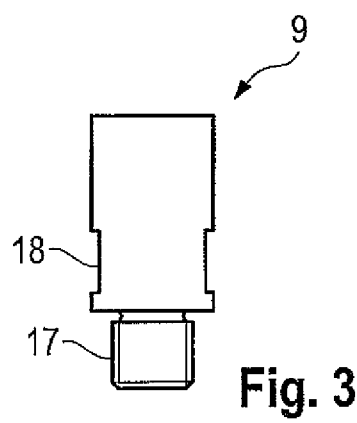
FIG. 3 shows a possible embodiment of a wearing body.
Figure 4:
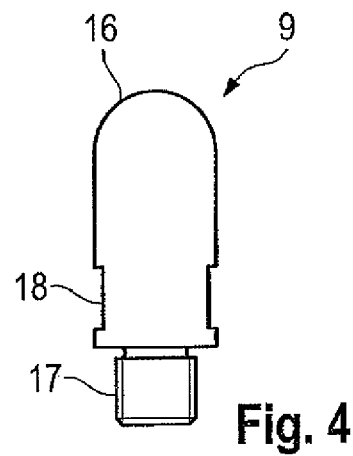
FIG. 4 shows a further possible embodiment of the wearing body.
Figure 5:
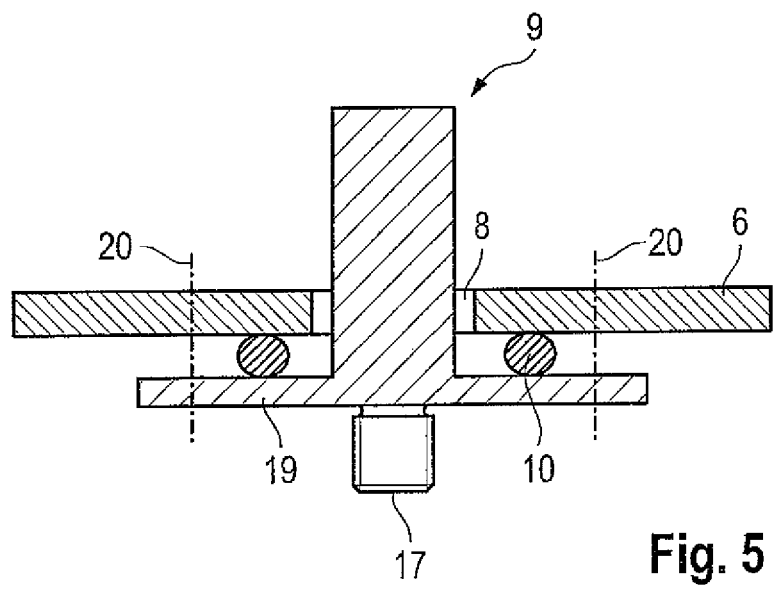
FIG. 5 shows a further alternative embodiment of the wearing body.

Three possible preferred embodiments of the sonotrode 9 can be seen in the illustrations of FIGS. 3, 4, and 5. In the illustration of FIG. 3, it is implemented as a cylinder, in the illustration 4, this cylinder has a spherical embodiment 16 on its end facing away from the ultrasound generator 11. In both cases, the sonotrodes 9 have a receptacle element 17 for connecting the sonotrode 9 to the ultrasound generator 11, which is not shown in the illustrations of FIGS. 3, 4, and 5. In addition, both sonotrodes 9 have a receptacle 18, for example, for a suitable adjustable wrench for screwing the sonotrode 9 using its receptacle 17, which is implemented as a thread, into the ultrasound generator 11. These two types of sonotrodes 9 are very robust in particular in relation to larger interfering parts, for example, rocks or branches, which possibly strike against the sonotrode 9. They are therefore to be understood as preferred embodiments, which are particularly well suitable for use in the device 7 according to the invention. The sonotrode 9 shown in FIG. 5 is particularly favorable with respect to the installation in the suction pipe wall 6 and with respect to the sealing. It has a flange 19. The seal 10 already shown in FIG. 2 is also located between the flange 19 and the suction pipe wall 8. An indicated screw connection 20 can then be provided outside the seal, in order to place the sonotrode 9 in the opening 8 of the suction pipe wall 6 to form a seal. The sonotrode 9 is then also easily accessible during operation and can be replaced if needed.

The sonotrodes 9 can have frontal incident flow or, as schematically indicated in the illustration of FIG. 2, lateral incident flow. In both cases, abrasive wear occurs in the region of the sonotrode 9, whereby it loses mass. The resonant frequency of the sonotrode 9, which is connected to the ultrasound generator 11, detected by the measuring unit 13 will then increase accordingly. The increasing resonant frequency is a measure of the abrasive wear, which becomes greater in the region of the sonotrode 9, and therefore indirectly also for the wear in the region of the water turbine 2.

The invention claimed is:

1. A device for detecting abrasive wear on components of water turbines, the device comprising:
   a wearing body; and
   a measuring unit for detecting the abrasive wear on the wearing body;
   wherein:
   the wearing body is arranged in a flow flowing through the water turbine;
   the wearing body is implemented as a sonotrode and is connected to an ultrasound generator; and
   the measuring unit is implemented to measure the resonant frequency of the sonotrode.

2. The device according to claim 1, wherein the sonotrode protrudes into the flow flowing out of the water turbine.

3. The device according to claim 2, wherein the sonotrode is implemented as a cylindrical wearing body having an attachment element for the connection to the ultrasound generator.

4. The device according to claim 3, wherein the sonotrode is shaped spherical on its side facing away from the ultrasound generator.

5. The device according to claim 2, wherein the sonotrode is shaped spherical on its side facing away from the ultrasound generator.

6. The device according to claim 2, wherein the sonotrode consists of a steel material, in particular a chromium-nickel steel or chromium-nickel-molybdenum steel.

7. The device according to claim 1, wherein the sonotrode is implemented as a cylindrical wearing body having an attachment element for the connection to the ultrasound generator.

8. The device according to claim 7, wherein the sonotrode is shaped spherical on its side facing away from the ultrasound generator.

9. The device according to claim 1, wherein the sonotrode is shaped spherical on its side facing away from the ultrasound generator.

10. The device according to claim 1, wherein the sonotrode consists of a steel material, in particular a chromium-nickel steel or chromium-nickel-molybdenum steel.

11. The device according to claim 1, wherein the sonotrode is implemented from a nonferrous material, in particular from an aluminum alloy or copper alloy.

12. The device according to claim 1, wherein the sonotrode is at least partially provided with a carbide coating.

13. A hydroelectric plant comprising:
   at least one water turbine, which is arranged between a pressure pipe in the flow direction upstream of the water turbine and a suction pipe in the flow direction downstream of the water turbine; and
   at least one device for detecting the abrasive wear according to claim 1.

14. The hydroelectric plant according to claim 13, wherein the sonotrode of the device is arranged in the suction pipe.

15. The hydroelectric plant according to claim 14, wherein the sonotrode protrudes through an opening in the suction pipe and is sealed in relation to the opening.

16. The hydroelectric plant according to claim 13, wherein the sonotrode is arranged downstream of a flow divider.

17. The hydroelectric plant according to claim 13, wherein the sonotrode is arranged in a pipe section, through which the flow flows, within or parallel to the suction pipe.

18. The hydroelectric plant according to claim 17, wherein the pipe section is implemented within the suction pipe as a half pipe and is fastened on the wall of the suction pipe.

19. A method for detecting the abrasive wear in a hydroelectric plant according to claim 13, wherein the resonant frequency of the sonotrode is measured by means of the measuring unit, wherein a resonant frequency which rises as a result of the material abrasion on the sonotrode is used as a measure for an increasing wear of components of the water turbine of the hydroelectric plant.

20. The method according to claim 19, wherein a measuring signal, which is correlated with the wear, is transmitted to a remote maintenance unit.

\* \* \* \* \*